US011096803B2

(12) United States Patent
Hsu et al.

(10) Patent No.: US 11,096,803 B2
(45) Date of Patent: Aug. 24, 2021

(54) MOVABLE JOINT FOR USE IN A PROSTHETIC OR ORTHOPEDIC SYSTEM

(71) Applicant: Ossur Iceland ehf, Reykjavik (IS)

(72) Inventors: Henry Hsu, Foothill Ranch, CA (US); Sigurdur Ásgeirsson, Foothill Ranch, CA (US)

(73) Assignee: OSSUR ICELAND EHF, Reykjavik (IS)

( * ) Notice: Subject to any disclaimer, the term of this patent is extended or adjusted under 35 U.S.C. 154(b) by 389 days.

(21) Appl. No.: 15/833,116

(22) Filed: Dec. 6, 2017

(65) Prior Publication Data

US 2018/0153711 A1    Jun. 7, 2018

Related U.S. Application Data

(60) Provisional application No. 62/430,629, filed on Dec. 6, 2016.

(51) Int. Cl.
*A61F 2/66* (2006.01)
*A61F 5/01* (2006.01)
(Continued)

(52) U.S. Cl.
CPC .............. *A61F 2/6607* (2013.01); *A61F 2/66* (2013.01); *A61F 2/70* (2013.01); *A61F 2/64* (2013.01); *A61F 2/76* (2013.01); *A61F 5/0109* (2013.01); *A61F 5/0125* (2013.01); *A61F 2002/5018* (2013.01); *A61F 2002/5021* (2013.01); *A61F 2002/6614* (2013.01); *A61F 2002/6836* (2013.01); *A61F 2002/74* (2013.01);
(Continued)

(58) Field of Classification Search
CPC .... A61F 2/60; A61F 2/64; A61F 2/604; A61F 2/68; A61F 2/66; A61F 2/6607; A61F 2/74; A61F 5/0125; A61F 5/0109
See application file for complete search history.

(56) References Cited

U.S. PATENT DOCUMENTS 2,638,605 A * 5/1953 Johnson ................. A61F 2/604
623/39
3,901,223 A    8/1975 May
(Continued)

FOREIGN PATENT DOCUMENTS

AU    2005203062 A1    8/2005
DE    29823435 U1    7/1999
(Continued)

OTHER PUBLICATIONS

International Search Report from PCT Application No. PCT/US2017/064827, dated Feb. 26, 2018.
(Continued)

*Primary Examiner* — Marcia L Watkins
(74) *Attorney, Agent, or Firm* — Workman Nydegger

(57) ABSTRACT

A movable joint for use in a prosthetic or orthopedic system includes first and second joint sections arranged to rotate relative to one another. At least one shaft member is attached to and arranged to rotate relative to the first or second joint sections. A translating member is attached to the at least one shaft member. Translation of the translating member along a length of the at least one shaft member drives rotation of at least the first joint section and the second joint section.

9 Claims, 9 Drawing Sheets

(51) Int. Cl.
*A61F 2/74* (2006.01)
*A61F 2/68* (2006.01)
*A61F 2/70* (2006.01)
*A61F 2/64* (2006.01)
*A61F 2/76* (2006.01)
*A61F 2/50* (2006.01)

(52) U.S. Cl.
CPC ............... *A61F 2005/0146* (2013.01); *A61F 2005/0158* (2013.01); *A61F 2005/0165* (2013.01)

(56) References Cited

U.S. PATENT DOCUMENTS

| | | |
|---|---|---|
| 3,902,482 A | 9/1975 | Taylor |
| 3,923,047 A | 12/1975 | Chant |
| 4,088,130 A | 5/1978 | Applegate |
| 4,493,316 A | 1/1985 | Reed et al. |
| 4,520,804 A | 6/1985 | DiGeorge |
| 4,524,764 A | 6/1985 | Miller et al. |
| 4,599,998 A | 7/1986 | Castillo |
| 4,614,454 A | 9/1986 | Kassai |
| 4,633,867 A | 1/1987 | Kausek et al. |
| 4,723,539 A | 2/1988 | Townsend |
| 4,732,143 A | 3/1988 | Kausek et al. |
| 4,791,916 A | 12/1988 | Paez |
| 4,802,372 A | 2/1989 | Harrod et al. |
| 4,821,707 A | 4/1989 | Audette |
| 4,856,501 A | 8/1989 | Castillo et al. |
| 4,886,054 A | 12/1989 | Castillo et al. |
| 4,890,607 A | 1/1990 | Townsend |
| 4,940,044 A | 7/1990 | Castillo |
| 4,961,416 A | 10/1990 | Moore et al. |
| 4,966,133 A | 10/1990 | Kausek |
| 4,986,264 A | 1/1991 | Miller |
| 4,991,571 A | 2/1991 | Kausek |
| 5,000,169 A | 3/1991 | Swicegood et al. |
| 5,022,391 A | 6/1991 | Weidenburner |
| 5,025,782 A | 6/1991 | Salerno |
| 5,031,606 A | 7/1991 | Ring, Sr. |
| 5,038,763 A | 8/1991 | Wiggins |
| 5,038,765 A | 8/1991 | Young et al. |
| 5,062,858 A | 11/1991 | Broeck et al. |
| 5,078,127 A | 1/1992 | Daneman et al. |
| 5,168,865 A | 12/1992 | Radcliffe et al. |
| 5,222,733 A | 6/1993 | Brunty |
| 5,230,696 A | 7/1993 | Silver et al. |
| 5,259,832 A | 11/1993 | Townsend et al. |
| 5,288,287 A | 2/1994 | Castillo et al. |
| 5,333,604 A | 8/1994 | Green et al. |
| 5,356,370 A | 10/1994 | Fleming |
| 5,372,572 A | 12/1994 | Tamagni |
| 5,376,134 A | 12/1994 | Biedermann |
| RE34,818 E | 1/1995 | Daneman et al. |
| 5,403,002 A | 4/1995 | Brunty |
| 5,443,444 A | 8/1995 | Pruyssers |
| 5,490,822 A | 2/1996 | Biedermann |
| 5,658,243 A | 8/1997 | Miller et al. |
| 5,662,596 A | 9/1997 | Young |
| 5,674,188 A | 10/1997 | Young |
| 5,741,221 A | 4/1998 | Wetz et al. |
| 5,766,140 A | 6/1998 | Tillinghast, III et al. |
| 5,772,618 A | 6/1998 | Mason et al. |
| 5,891,071 A | 4/1999 | Stearns et al. |
| 5,921,946 A | 7/1999 | Tillinghast et al. |
| 6,001,075 A | 12/1999 | Clemens et al. |
| 6,027,466 A | 2/2000 | Diefenbacher et al. |
| 6,074,355 A | 6/2000 | Bartlett |
| 6,129,689 A | 10/2000 | Dibello |
| 6,402,711 B1 | 6/2002 | Nauert |
| 6,676,617 B1 | 1/2004 | Miller |
| 6,736,567 B1 | 5/2004 | Dibello |
| 6,740,054 B2 | 5/2004 | Stearns |
| 6,752,775 B2 | 6/2004 | Seligman et al. |
| 6,890,314 B2 | 5/2005 | Seligman |
| 7,044,925 B2 | 5/2006 | Castillo et al. |
| 7,059,329 B2 | 6/2006 | Mason et al. |
| 7,189,212 B2 | 3/2007 | Popp et al. |
| 7,235,058 B2 | 6/2007 | Doty et al. |
| 7,507,215 B2 | 3/2009 | Ryan |
| 7,534,219 B2 | 5/2009 | Stearns |
| 7,544,174 B2 | 6/2009 | Nathanson |
| 7,578,799 B2 | 8/2009 | Thorsteinsson et al. |
| 7,662,119 B2 | 2/2010 | Detoro et al. |
| 7,682,322 B2 | 3/2010 | Engelman |
| 7,699,798 B2 | 4/2010 | Coligado |
| 7,722,555 B2 | 5/2010 | Doty et al. |
| 7,762,972 B2 | 7/2010 | Cho |
| 7,811,242 B2 | 10/2010 | Seligman |
| 7,967,765 B2 | 6/2011 | Nathanson |
| 7,985,193 B2 | 7/2011 | Thorsteinsson et al. |
| 8,043,243 B2 | 10/2011 | Nathanson et al. |
| 8,062,242 B2 | 11/2011 | Ceriani et al. |
| 8,202,325 B2 | 6/2012 | Albrecht-Laatsch et al. |
| 8,287,476 B2 | 10/2012 | Bettiol |
| 8,292,838 B2 | 10/2012 | Ingimundarson et al. |
| 8,795,212 B2 | 8/2014 | Seligman |
| 8,939,924 B1 | 1/2015 | Paulos |
| 9,125,730 B2 | 9/2015 | Ingimundarson et al. |
| 9,220,625 B2 | 12/2015 | Ingimundarson et al. |
| 2004/0054307 A1 | 3/2004 | Mason et al. |
| 2004/0097859 A1 | 5/2004 | Stearns |
| 2004/0167452 A1 | 8/2004 | Mason et al. |
| 2005/0148915 A1 | 7/2005 | Nathanson et al. |
| 2005/0148918 A1 | 7/2005 | Nathanson |
| 2005/0192523 A1 | 9/2005 | Knecht et al. |
| 2006/0009722 A1 | 1/2006 | Seligman |
| 2006/0173392 A1 | 8/2006 | Turrini et al. |
| 2006/0287624 A1 | 12/2006 | Popp et al. |
| 2008/0108922 A1 | 5/2008 | Castillo et al. |
| 2008/0188784 A1 | 8/2008 | Ceriani et al. |
| 2009/0030356 A1 | 1/2009 | Maloney |
| 2009/0182254 A1 | 7/2009 | Cho |
| 2009/0299244 A1 | 12/2009 | Chiang et al. |
| 2010/0049108 A1 | 2/2010 | Napholz |
| 2010/0286579 A1 | 11/2010 | Bettiol |
| 2011/0152736 A1 | 6/2011 | Ng |
| 2012/0059296 A1 | 3/2012 | Kompa |
| 2012/0271211 A1 | 10/2012 | Bledsoe |
| 2013/0331754 A1 | 12/2013 | Dunn et al. |
| 2014/0207040 A1 | 7/2014 | Ingimundarson et al. |
| 2014/0330393 A1 | 11/2014 | Ward et al. |
| 2015/0223958 A1 | 8/2015 | Dunn |
| 2015/0374530 A1 | 12/2015 | Bosshard et al. |
| 2016/0008157 A1 | 1/2016 | Brookover et al. |
| 2016/0278947 A1 | 9/2016 | Martin |
| 2017/0119569 A1 | 5/2017 | Hsu et al. |

FOREIGN PATENT DOCUMENTS

| | | |
|---|---|---|
| EP | 0327286 A2 | 8/1989 |
| EP | 0413424 A1 | 2/1991 |
| EP | 0454186 A2 | 10/1991 |
| EP | 0546330 A1 | 6/1993 |
| EP | 0615737 A1 | 9/1994 |
| EP | 0693276 A1 | 1/1996 |
| EP | 0382976 A1 | 8/1999 |
| EP | 1010409 A1 | 6/2000 |
| EP | 1388330 A1 | 2/2004 |
| EP | 1639970 A2 | 3/2006 |
| EP | 2345393 A1 | 7/2011 |
| EP | 2823792 A1 | 1/2015 |
| GB | 190626961 A | 4/1907 |
| WO | 9014807 A1 | 12/1990 |
| WO | 99/39668 A1 | 8/1999 |
| WO | 01/10360 A1 | 2/2001 |
| WO | 2004/078078 A1 | 9/2004 |
| WO | 2009/092798 A1 | 7/2009 |
| WO | 2014/067698 A1 | 5/2014 |
| WO | 2015157723 A1 | 10/2015 |
| WO | 2016100791 A1 | 6/2016 |

(56) References Cited

OTHER PUBLICATIONS

International Search Report and Written Opinion from PCT Application No. PCT/US2013/043322, dated Aug. 20, 2013.
International Search Report and Written Opinion from PCT Application No. PCT/US2015/015358, dated Apr. 22, 2015.
International Search Report from PCT Application No. PCT/US2015/061480, dated Apr. 4, 2016.
International Search Report from PCT Application No. PCT/US2016/059005, dated Jan. 5, 2017.
International Search Report From PCT Application No. PCT/US2017/027147, dated Jun. 26, 2017.

* cited by examiner

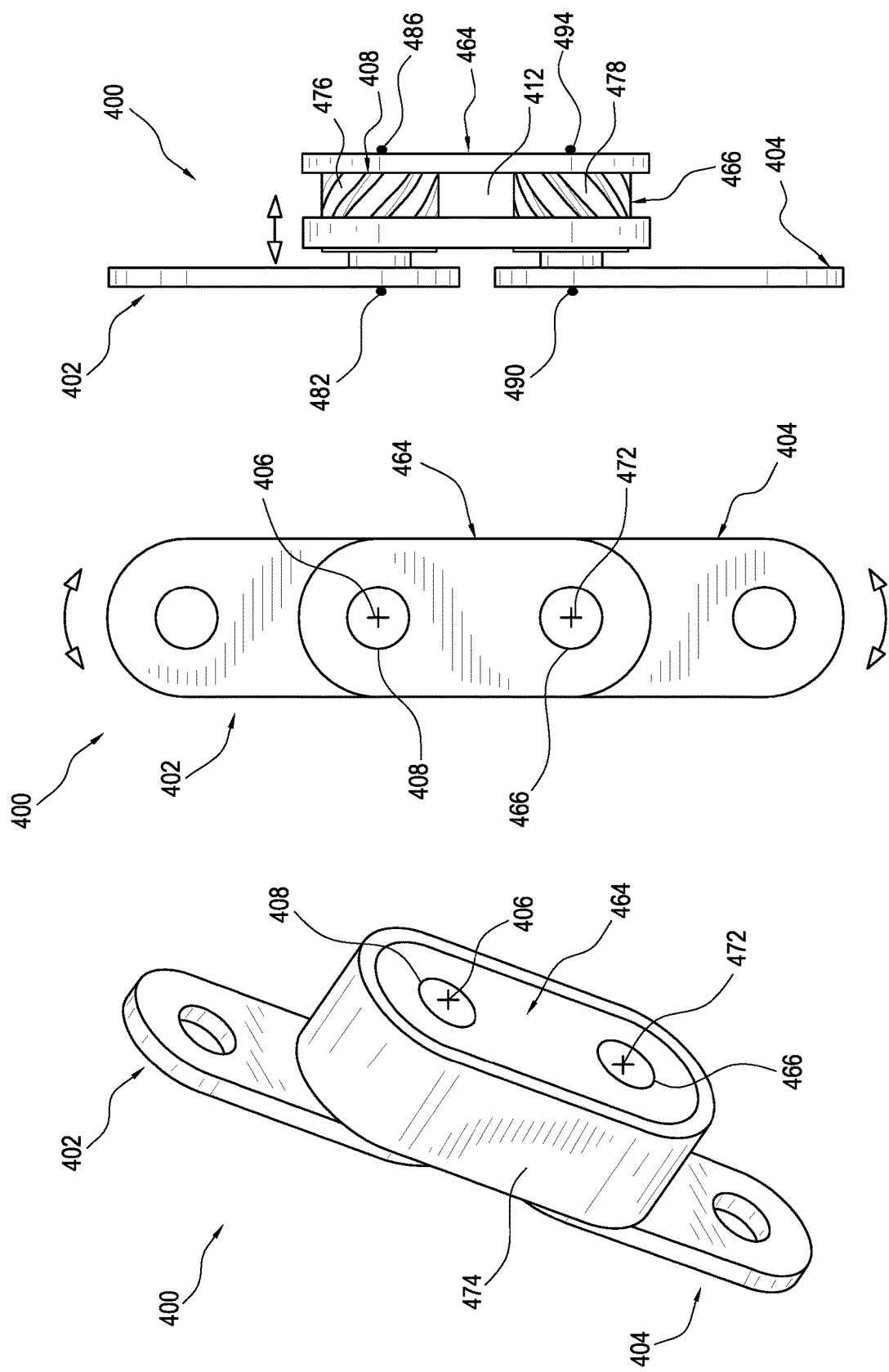

MOVABLE JOINT FOR USE IN A PROSTHETIC OR ORTHOPEDIC SYSTEM

BACKGROUND

Many conventional prosthetic systems require at least one movable joint for controlling, supporting, immobilizing, replacing, or treating muscles, joints, or skeletal parts, which are weak, ineffective, deformed, missing, or injured.

There are many types of movable joints that can be used in prosthetic systems. For instance, to assist in restoring a human joint to normal, effective function, it may be prescribed by a clinician that the joint be restricted for a period by an orthopedic device including at least one movable joint in the form of a hinge which imposes a fixed pivoted position on the joint. Or an orthopedic device may be needed that permits adjustable angular displacement of the joint, which is retained for a period of time by the orthopedic device and gradually increased to improve the pivotal range of use.

While commercially available movable joint products exist, many of these movable joints are complicated in design, bulky, and fail to provide sufficient motion control. They are also known to fail or undesirably move from a locked pivoted position set by a clinician, increasing the likelihood of injury to a patient. Furthermore, many movable joint products are not capable of providing continuous angular adjustment, and are difficult to adjust while being worn.

It can be seen from the foregoing there are many needs for improving on the drawbacks of conventional movable joints. The embodiments of the present disclosure address many of these aforementioned shortcomings.

SUMMARY

Embodiments of this disclosure describe a movable joint providing a simplified construction and design that facilitates greater control of movement and stronger support for orthopedic and prosthetic devices. According to a variation, the movable joint includes first and second joint sections arranged to rotate relative to one another. At least one shaft member is attached to the first or second joint sections and arranged to rotate relative to at least one of the first and second joint sections. A translating member is attached to the at least one shaft member.

To adjust the angular position between the first and second joint sections, the at least one shaft member can be rotated relative to at least one of the joint sections. This rotation causes the translating member to translate along the at least one shaft member, which, in turn, causes at least one of the joint sections to pivot relative to the other joint section. Rotation of the shaft member thus advantageously controls and drives rotation of the joint sections via translation of the translating member.

According to a variation, the movable joint can include an actuator arranged to provide the movable joint with energy to execute angular displacements between the first and second joint sections. For instance, the first joint section can comprise a lower limb member and the second joint section can comprise a foot unit, and the actuator can be arranged to controllably drive rotation of the at least one shaft member, which, in turn, can move the foot unit similar to a natural human foot. The actuator can also help control or actively adjust the angle between the lower limb member and the foot unit.

Moreover, the interaction between the translating member and the at least one shaft member can be arranged such that the actuator can continuously adjust the movable joint within a range of motion defined by the movable joint, providing greater control of movement and functionality.

In an embodiment, because of shear friction and/or a high mechanical advantage of the movable joint, the movable joint can be self-locking. In other words, an input force or torque applied to the second joint section will not move the second joint section, the translating member, or the at least one shaft member. Thus, whatever angle is set between the joint sections by the at least one shaft member remains substantially fixed until the shaft member is readjusted. In addition, the self-locking configuration of the movable joint allows the hinge assembly to be locked and/or unlocked under a load, increasing safety and ease of use.

BRIEF DESCRIPTION OF THE DRAWINGS

These and other features, aspects, and advantages of the present disclosure will become better understood regarding the following description, appended claims, and accompanying drawings.

FIG. 10 is a perspective view of a movable joint according to another embodiment.

FIG. 11 is a side view of the movable joint in FIG. 10.

FIG. 12 is a front view of the movable joint in FIG. 10.

DETAILED DESCRIPTION OF VARIOUS EMBODIMENTS

Figure 1:
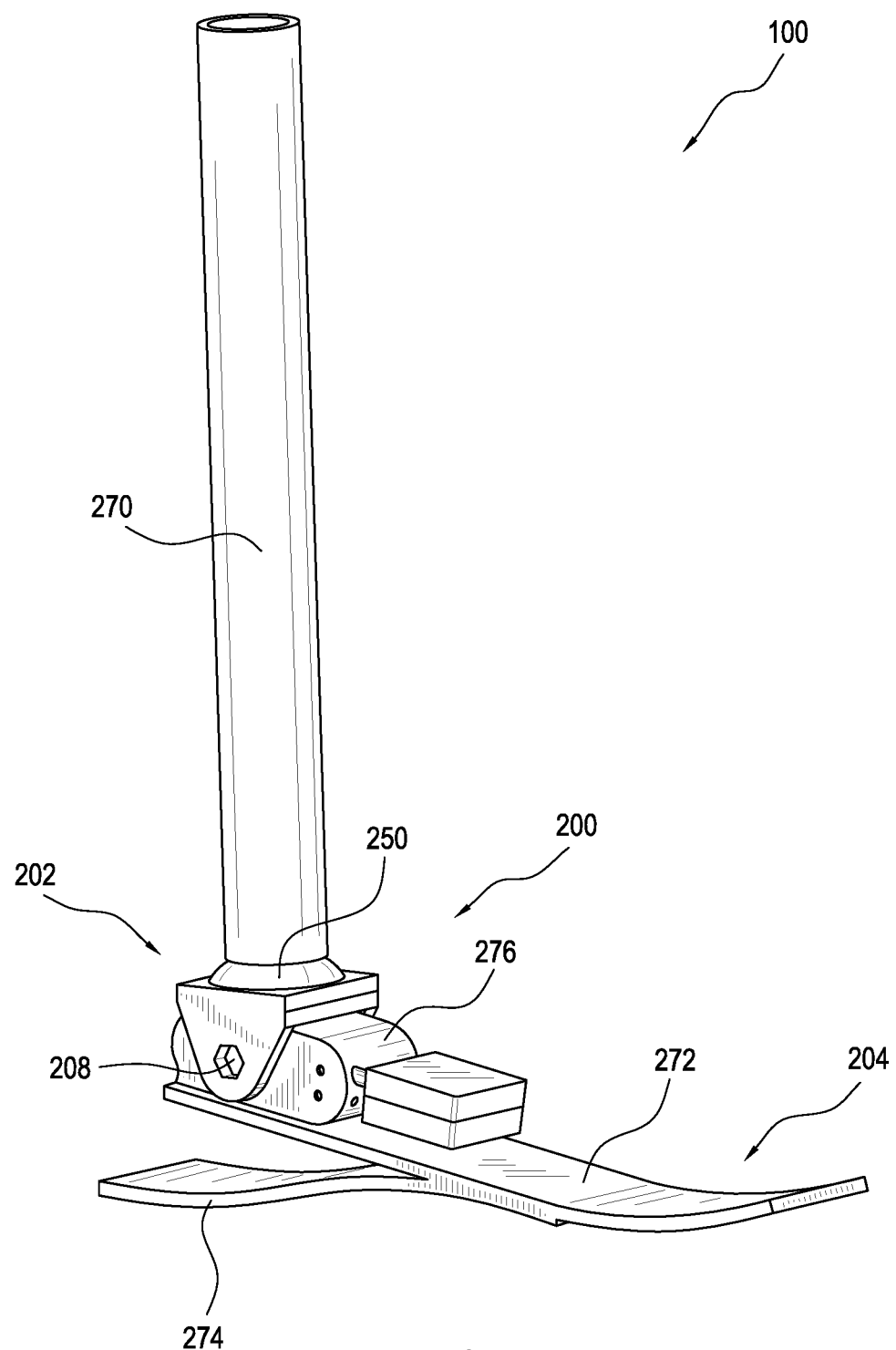
FIG. 1 is a perspective view of a prosthetic system including a movable joint according to an embodiment.

A better understanding of different embodiments of the disclosure may be had from the following description read with the accompanying drawings in which like reference characters refer to like elements.

While the disclosure is susceptible to various modifications and alternative constructions, certain illustrative embodiments are in the drawings and are described below. It should be understood, however, there is no intention to limit the disclosure to the specific embodiments disclosed, but on the contrary, the intention covers all modifications, alternative constructions, combinations, and equivalents falling within the spirit and scope of the disclosure.

It will be understood that unless a term is expressly defined in this application to possess a described meaning, there is no intent to limit the meaning of such term, either expressly or indirectly, beyond its plain or ordinary meaning.

The movable joint embodiments described are configured for use with a prosthetic ankle and prosthetic knee. It should be remembered, however, that the same concepts and methods described may be similarly used for other prostheses and orthopedic devices and are not limited solely to the anatomical locations discussed.

Any element in a claim that does not explicitly state "means for" performing a specified function, or "step for" performing a specific function is not to be interpreted as a "means" or "step" clause as specified in 35 U.S.C. § 112, paragraph 6.

As shown in FIGS. 1-5, embodiments of the movable joint can be employed with a prosthesis 100. The prosthesis 100 includes a movable joint 200 having a first joint section comprising a lower limb member 202, operatively coupled to a second joint section comprising a foot unit 204. The lower limb member 202 can be any member that attaches either directly or indirectly to the foot unit 204 and is moveable in relation thereto, for example by a pivoting motion, and is used to attach the prosthesis 100 to a stump or intermediate prosthesis.

The lower limb member 202 can be generally formed of a metal, such as aluminum, or a carbon fiber material. In other embodiments, the lower limb member 202 may include other materials that are suitable for prosthetic devices. The lower limb member 202 includes an attachment portion 250 to facilitate coupling of the lower limb member 202. For instance, the attachment portion 250 can couple the lower limb member 202 to a pylon 270. In other embodiments, the attachment portion 250 can be configured to couple the prosthesis 100 to a stump of an amputee or to another prosthetic device. Optionally, the lower limb member 202 may include a cover that houses and/or protects the lower limb member 202.

The foot unit 204 can comprise various types of prosthetic feet. For instance, the foot unit 204 may comprise a foot member 272 that extends from a proximal section terminating at a proximal end to a distal section terminating at a distal end. A heel member 274 can extend rearwardly from the foot member 272 and is disposed below at least a portion of the foot member 272. The heel member 274 can have a curvilinear profile along its length.

In other embodiments, the foot unit 204 may comprise a split-toe configuration, which facilitates movement on uneven terrain. The foot unit 204 may also include a cosmesis or a foot cover such as, for example, a standard Flex-Foot cover available from Ossur.

Figure 2:
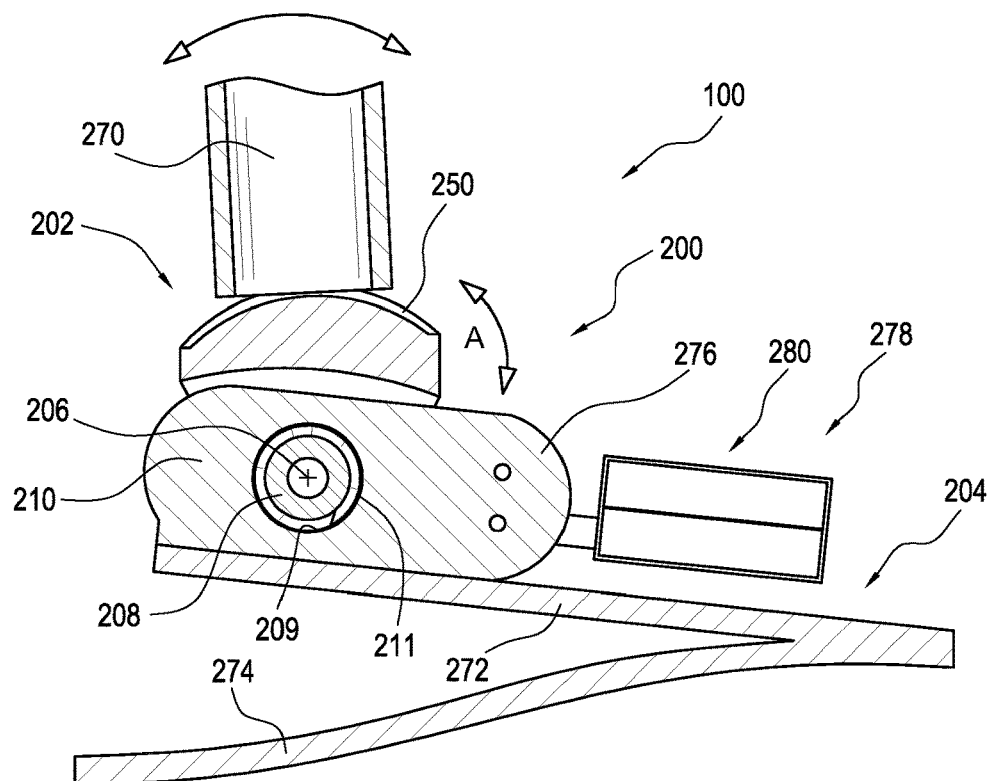
FIG. 2 is a cross section view of the movable joint in FIG. 1.

As shown, the lower limb member 202 is coupled to the foot unit 204 at a pivot point 206 (shown in FIG. 2). The pivot point 206 allows for angular movement of the foot unit 204 with respect to the lower limb member 202. The pivot point 206 can be defined by at least one shaft member 208. The shaft member 208 can be located on a same axis as the pivot point 206.

The shaft member 208 can be non-rotatably attached to the lower limb member 202. In other embodiments, the shaft member 208 can be non-rotatably attached to the foot unit 204. The pivot point 206 can comprise a hinge, a multiaxial configuration, a polycentric configuration, combinations of the same, or the like. The shaft member 208 can be located on a portion of the prosthesis 100 that is near a natural ankle location of the foot unit 204. In other embodiments, the shaft member 208 may be bolted or otherwise releasably connected to the foot unit 204 or the lower limb member 202.

Figure 3:
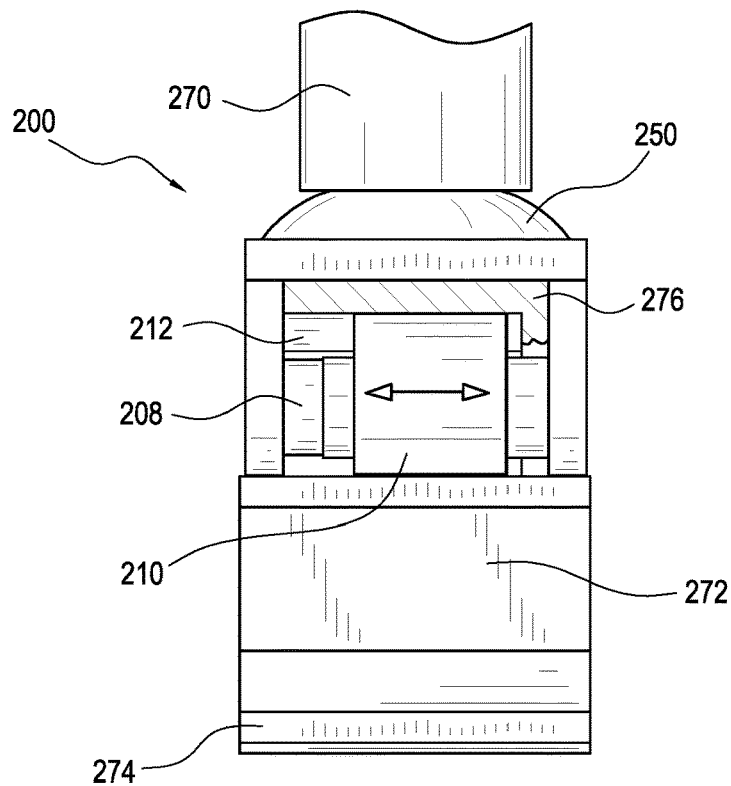
FIG. 3 is a back view of the movable joint in FIG. 1.

As seen in FIGS. 2 and 3, a translating member 210 is threadedly attached to the shaft member 208. The translating member 210 is positioned within a receiving space 212 defined by a housing 276 attached to the foot unit 204. The translating member 210 is restrained from rotation so that translation of the translating member 210 results in rotation of the shaft member 208, which, in turn, rotates the lower limb member 202.

The operation of the prosthesis 100 according to an embodiment will now be described. When the translating member 210 translates in a first direction along a length of the shaft member 208 within the housing 276, the interaction between the translating member 210 and the shaft member 208 causes or drives the shaft member 208 to rotate in a counter-clockwise direction about the pivot point 206, which, in turn, adjusts the angle A between the lower limb member 202 and the foot unit 204. In an embodiment, this adjustment can bring the angle A between the lower limb member 202 and the foot unit 204 to a dorsiflexed position.

When the translating member 210 translates in a second direction opposite the first direction along a length of the shaft member 208, the interaction between the translating member 210 and the shaft member 208 causes or drives the shaft member 208 to rotate in a clockwise direction about the pivot point 206, which, in turn, adjusts the angle A between the lower limb member 202 and the foot unit 204. In an embodiment, this adjustment can bring the angle A between the lower limb member 202 and the foot unit 204 to a plantar flexion position.

Axial movement of the translating member 210 along the shaft member 208 thus advantageously controls and/or drives relative rotation between the lower limb member 202 and the foot unit 204. As described in more detail below, a large contact surface area is defined between the shaft member 208 and the translating member 210 and the housing 276 of the foot unit 204. This allows the prosthesis 100 to distribute and handle greater loads than prior art prostheses. It can also allow the prosthesis 100 to be made smaller and/or simpler than in the prior art. This can result in prostheses that are less bulky, lighter-weight, and more natural to wear.

In an embodiment, the prosthesis 100 can include an actuator 278 arranged to provide the prosthesis 100 with energy to execute angular displacements between the lower limb member 202 and the foot unit 204. For instance, the actuator 278 can be arranged to controllably drive rotation of the shaft member 208, which, in turn, can move the foot unit 204 to move similar to a natural human foot. The actuator 278 can also help control or actively adjust the angle between the lower limb member 202 and the foot unit 204. Moreover, the interaction between the translating member 210 and the shaft member 208 can be arranged such that the actuator 278 can continuously adjust the movable joint within a range of motion defined by the prosthesis 100.

The actuator 278 can be any suitable drive system but is shown as a pump system 280 arranged to drive translation of the translating member 210 within the housing 276 along the shaft member 208 in the first and/or second directions, which, in turn, drives rotation of the foot unit 204 relative to the lower limb member 202.

Figure 4:
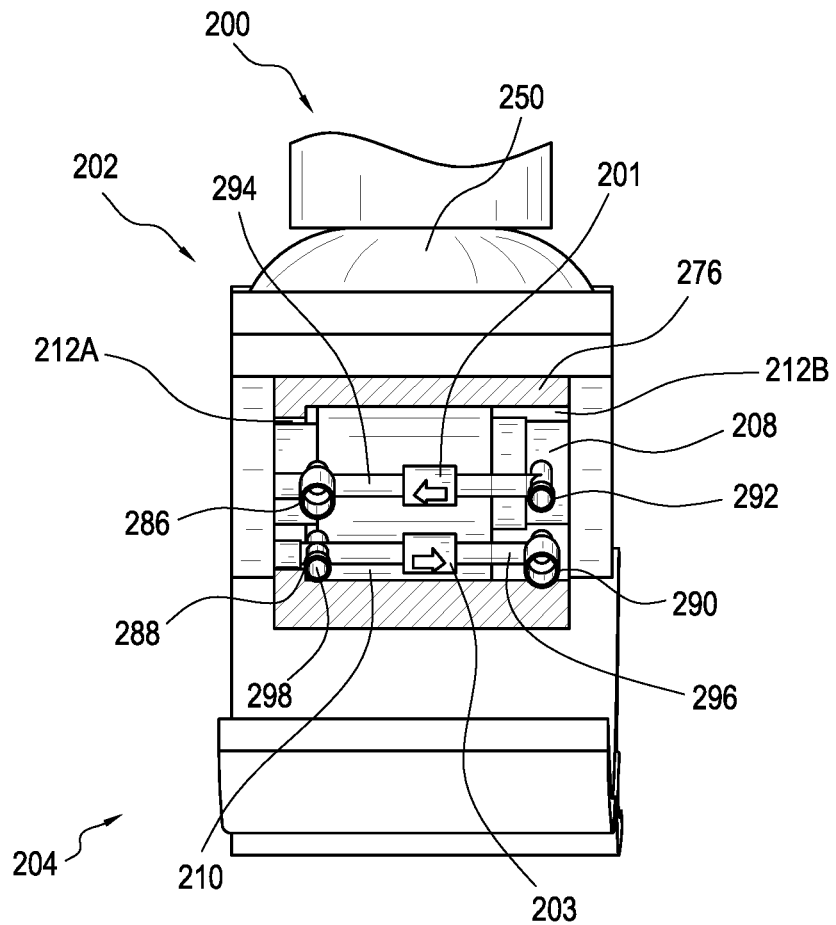
FIG. 4 is a partial cutaway view of the movable joint in FIG. 1.
Figure 5B:
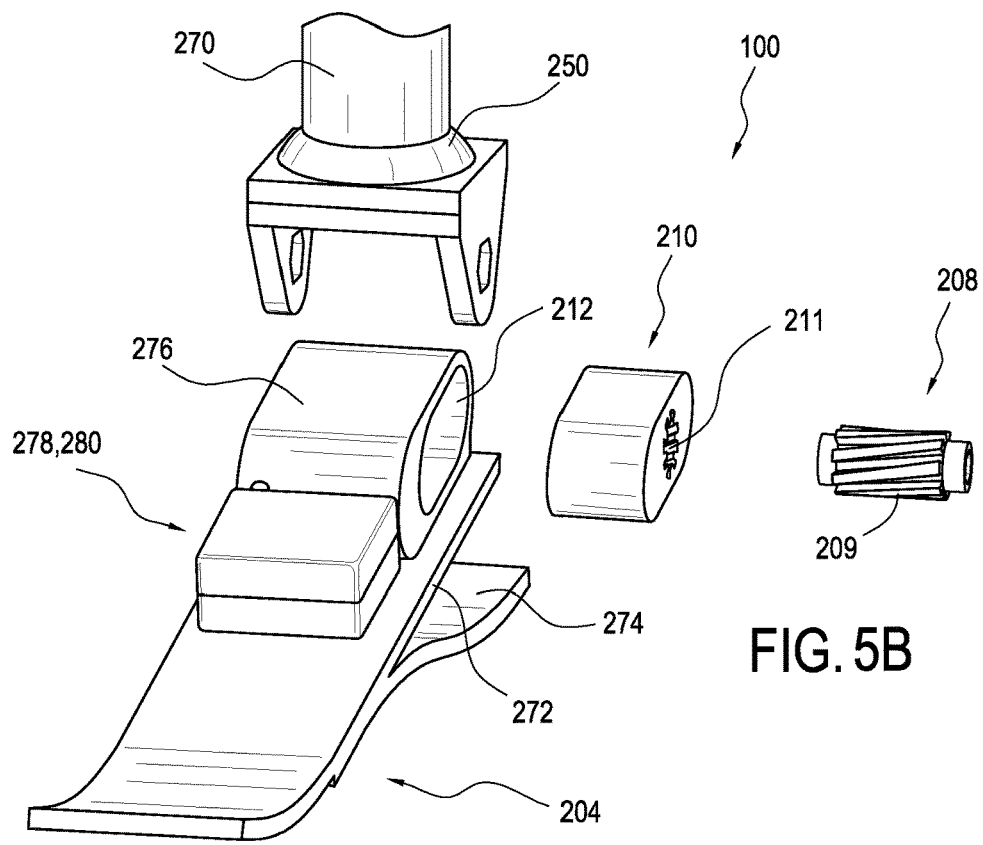
FIG. 5B is another partial exploded view of the movable joint in FIG. 1.
Figure 5A:
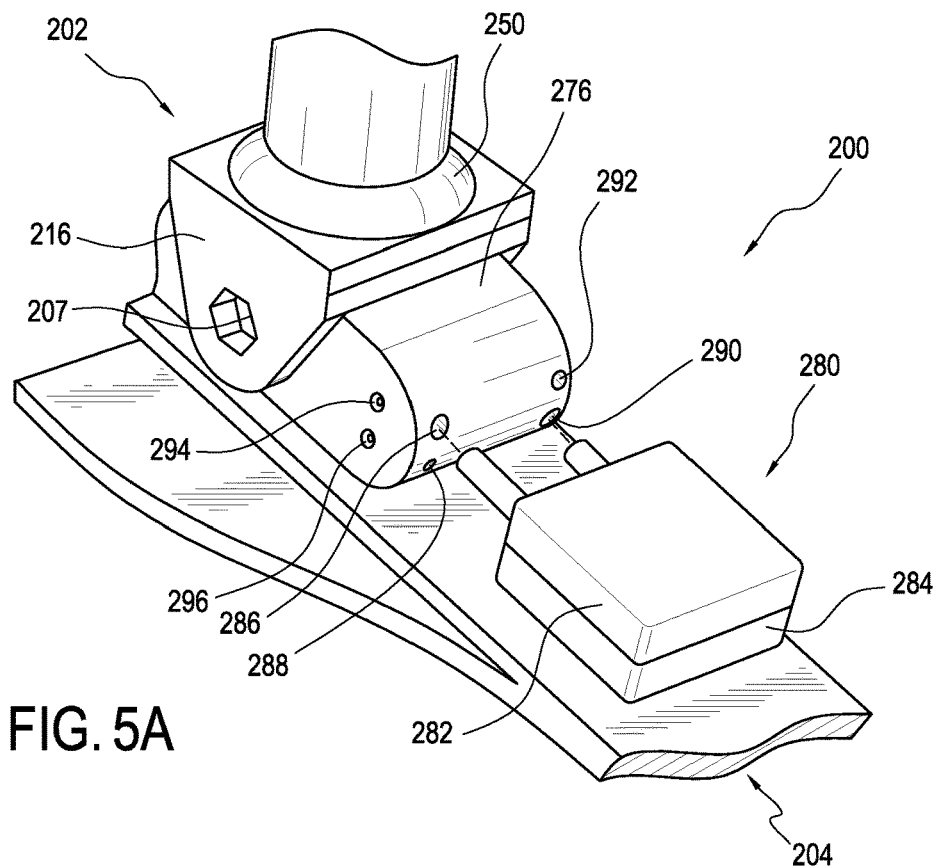
FIG. 5A is a partial exploded view of the movable joint in FIG. 1.
Figure 6:
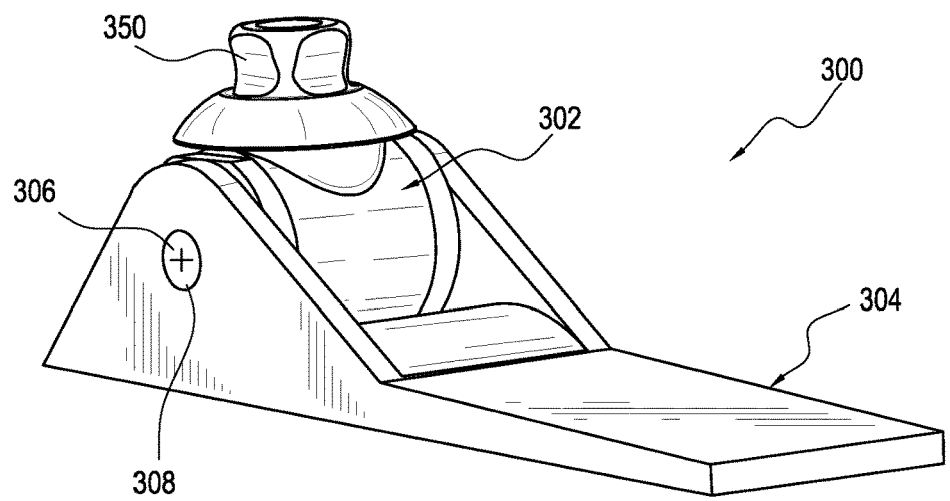
FIG. 6 is a perspective view of a movable joint according to another embodiment.
Figure 7:
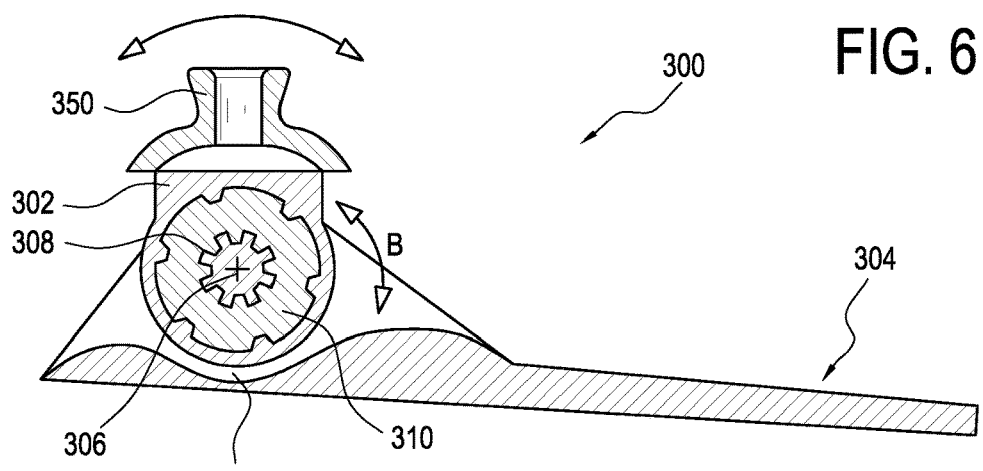
FIG. 7 is a cross section of the movable joint in FIG. 6.

As best seen in FIGS. 4 and 5A, the pump system 280 can include a first pump unit 282 and a second pump unit 284, and the receiving space 212 can define a first fluid chamber 212A on a first side of the translating member 210 and a second fluid chamber 212B on a second side of the translating member 210 opposite the first side of the translating member 210. The housing 276 defines first and second openings 286, 288 in fluid communication with the first fluid chamber 212A and third and fourth openings 290, 292 in fluid communication with the second fluid chamber 212B. The first pump unit 282 is fluidly attachable to the first opening 286 and the second pump unit 284 is fluidly attachable to the third opening 290.

When the first and second pump units 282, 284 are attached to the housing 276, the fluid chambers 212A, 212B and the passageways 294, 296 can at least in part define a sealed volume arranged to contain a fluid. The fluid can comprise hydraulic fluid and/or any other suitable type of fluid.

According to a variation, one or more plug members 298 can be removably inserted in the second and third openings 288, 294 and/or the first and second passageways 294, 296. This advantageously allows fluid in the sealed volume to be changed, added and/or removed from the fluid chambers 212A, 212B via the second and third openings 288, 294 and/or the first and second passageways 294, 296. In other embodiments, the second and third openings 288, 294 and/or the first and second passageways 294, 296 can be defined entirely within the housing 276.

A first passageway 294 is defined in the housing 276 that extends between the first opening 286 and the fourth opening 292. A second passageway 296 is defined in the housing 276 that extends between the second opening 288 and the third opening 290. In an embodiment, the housing 276 contains two valve assemblies 201, 203. The valve assemblies can include a one-way valve, also referred to as a check valve. A preferred type of one-way valve is a duckbill valve. It should be appreciated however that other types of one-way valves are possible.

The valve assembly 201 can be positioned in the first passageway 294 and arranged to only allow fluid to exit the second fluid chamber 212B and enter the first fluid chamber 212A via the first passageway 294. The valve assembly 203 can be positioned in the second passageway 296 and arranged to only allow fluid to exit the first fluid chamber 212A and enter the second fluid chamber 212B via the second passageway 296.

When the pump system 280 is attached to the housing 276, the first pump unit 282 can drive fluid in the first fluid chamber 212A via the first opening 286. This driving force on the fluid increases pressure within the first fluid chamber 212A, which, in turn, drives the translating member 210 in a first direction along the shaft member 208. This translation of the translating member 210 drives rotation of the shaft member 208 in a first rotational direction, which, in turn, drives rotation of the lower limb member 202 about the pivot point 206 in the first rotational direction. The valve assembly 203 is arranged to release fluid from the first fluid chamber 212A into the second fluid chamber 212B. This can be done in response to a control signal from a control system in communication with the valve assembly 203. This can be done automatically when the pressure within the first fluid chamber 212A exceeds a cracking pressure of the valve assembly 203.

When the fluid is in the second fluid chamber 212B, the second pump unit 284 can drive the fluid in the second fluid chamber 212B via the third opening 290. This driving force on the fluid increases the pressure within the second fluid chamber 212B, which, in turn, drives the translating member 210 in a second direction along the shaft member 208 opposite the first direction. This translation of the translating member 210 drives rotation of the lower limb member 202 about the pivot point 206 in a second rotational direction opposite the first rotation direction, which, in turn, drives rotation of the lower limb member 202 about the pivot point 206 in the second rotational direction. The valve assembly 201 is arranged to release fluid from the second fluid chamber 212B into the first fluid chamber 212A. This can be done via a control system or automatically when the pressure in the second fluid chamber 212B exceeds a cracking pressure of the valve assembly 201. The pump system 280 can thus advantageously control rotational movement of the movable joint 200 via controlled or selective pressurization of the fluid in the fluid chambers 212A, 212B.

While the actuator 278 is described as a pump system, in other embodiments, the actuator may comprise other drive systems capable of actively adjusting an angle, or providing for motion between, multiple members. For example, the actuator may comprise a single-screw motor, a double-screw motor, a servomotor, a servo valve, a stepper motor, a rotary motor, a spring, a threaded member, or the like.

Referring now to FIGS. 5A and 5B, the lower foot member 202 defines generally upstanding support arm portions 216 on opposite sides of the housing 276. A pair of opposing holes 207 are formed in the support arm portions 216. The support arm portions 216 are sized such that a clearance is formed between the lower limb member 202 and the upper surface of the foot unit 204 when the lower limb member 202 is attached to the housing 276.

The shaft member 208 is connected to the lower limb member 202 between the support arm portions 216. The shaft member 208 can be connected to the lower limb member 202 via the holes 207. The shaft member 208 can be connected to the support arm portions 216 so that the shaft member 208 and the lower limb member 202 rotate together.

In an embodiment, the shaft member 208 can define a plurality of teeth 209. The teeth 209 can be formed at an angle to the longitudinal axis of the shaft member 208. The teeth can extend completely or along one or more portions of the shaft member 208. The teeth can be generally helical.

The translating member 210 is attached to the shaft member 208 and positioned between the support arm portions 216 of the lower limb member 202. The translating member 210 is adapted to move axially along the length of the shaft member 208 along the teeth. The translating member 210 is dimensioned and configured such that it can move in a back and forth direction between the support arm portions 216.

The translating member 210 is shown having a stadium shaped body but can have any suitable shape. The translating member 210 can define an internal gear or teeth 211 along a bore defined by the translating member 210. The teeth 211 of the translating member 210 are arranged to mesh or interact with the teeth 209 of the shaft member 208. The teeth 211 of the translating member 210 can be generally helical. When the translating member 210 is positioned in the receiving space 212, the translating member 210 is arranged not to rotate. The teeth 209 and the teeth 211 can exhibit any suitable configuration.

Tooth loads between the translating member 210 and the shaft member 208 create a driving force when the translating member 210 translates to rotate the lower limb member 202. An upper surface of the lower limb member 202 can define a flat area for facilitating attachment of the attachment portion 250 to the lower limb member 202.

As the translating member 210 moves along the axis of the shaft member 208, the interaction or tooth load between the teeth 209, 211 of the two components generate the driving force that rotates the lower limb member 202 about the pivot point 206. Translation of the translating member 210 thus advantageously controls and/or drives rotation of the lower limb member 202.

The length, angle, depth, thickness, curvature, pressure angle, and/or pitch of the teeth and/or size of the translating member 210 and/or the lower limb member 202 can at least in part define a range of motion of the prosthesis 100 and/or the strength of the prosthesis 100 under a load.

When the teeth 211 of the translating member 210 are engaged with the teeth of the shaft member 208, they can be fully engaged, providing an increased area of thread engagement. In addition, the teeth 211 of the translating member 210 are distributed circumferentially about the shaft member 208. This provides a solid connection between the shaft member 208 and the translating member 210 by increasing the surface contact area between them. This increased surface contact area also allows the prosthesis 100 to support and/or distribute greater loads. It also facilitates control of the angular displacement between the foot unit 204 and the lower limb member 202. Similarly, the increased area of thread engagement between the translating member 210 and the lower limb member 202 allows the prosthesis 100 to distribute greater loads and facilitates better control of the angular displacement between the foot unit 204 and the lower limb member 202.

According to a variation, the movable joint 200 is self-locking such that an input force applied to the lower limb member 202 will not move the foot unit 204. Furthermore, because rotation of the shaft member 208 and corresponding translation of the translating member 210 drives and controls rotation of the lower limb member 202, the movable joint 200 is continuously adjustable within a range of motion defined by the movable joint 200. This continuous adjustability in combination with the self-locking configuration of the prosthesis also allows the movable joint 200 to be locked or maintained in an infinite number of positions within the range of motion rather than only be lockable in discrete increments as in the prior art, providing greater control of movement and functionality.

In other embodiments, the movable joint 200 is not self-locking such that an input force applied to the lower limb member 202 will not rotate the foot unit 204 and an input force applied to the foot unit 202 will rotate the lower limb member 202.

FIGS. 6-9 illustrate another embodiment of a movable joint comprising a prosthesis 300. The prosthesis 300 comprises a first joint section comprising a lower limb member 302, operatively coupled to a second joint section comprising a foot unit 304. Similar to the lower limb member 202, the lower limb member 302 can be any member that attaches either directly or indirectly to the foot unit 304 and is moveable in relation thereto. The lower limb member 302 includes an attachment portion 350 to facilitate coupling of the lower limb member 302 to a prosthesis such as a pylon or prosthetic socket.

As shown, the lower limb member 302 is coupled to the foot unit 304 at a pivot point 306. The pivot point 306 allows for angular movement of the foot unit 304 with respect to the lower limb member 302. The pivot point 306 can be defined by at least one shaft member 308. The shaft member 308 can be located on a same axis as the pivot point 306.

The shaft member 308 can be non-rotatably attached to the foot unit 304. In other embodiments, the pivot point 306 comprises a hinge, a multiaxial configuration, a polycentric configuration, combinations of the same or the like. The shaft member 308 can be located on a portion of the foot unit 304 that is near a natural ankle location of the foot unit 304. In other embodiments, the shaft member 308 may be bolted or otherwise releasably connected to the foot unit 304.

A translating member 310 is attached to the shaft member 308. The translating member 310 is positioned within a receiving space 312 defined by the lower limb member 302. The translating member 310 is restrained from rotation so that rotation of the shaft member 308 results in translation of the translating member 310 along the shaft member 308. The translating member 310 also engages or meshes with the ankle member 302 so that translation of the translating member 310 results in rotation of the ankle member 302 about the pivot point 306.

Figure 8:
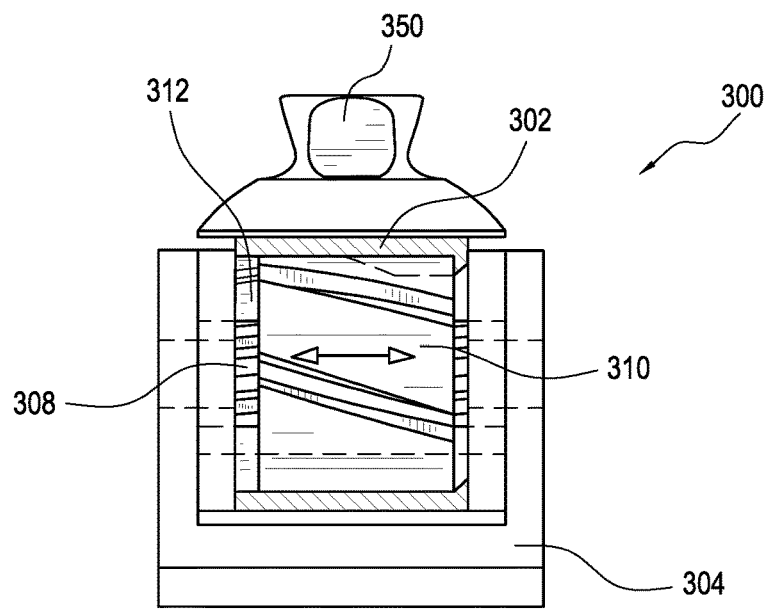
FIG. 8 is a partial cutaway view of the movable joint in FIG. 6.

The operation of the prosthesis 300 according to an embodiment will now be described. When the foot unit 304 is rotated in a clockwise direction from a neutral position, the shaft member 308 rotates with the foot unit 304 in the clockwise direction. This rotation of the shaft member 308 in the clockwise direction causes or drives the translating member 310 to translate in a first direction along a length of the shaft member 308 as shown in FIG. 8. The translation of the translating member 310 in the first direction in turn causes or drives the lower limb member 302 to rotate in a counter-clockwise direction about the pivot point 306, adjusting the angle B between the lower limb member 302 and the foot unit 304. In an embodiment, this adjustment can bring the angle B between the lower limb member 302 and the foot unit 304 to a dorsiflexed position.

When the foot unit 304 is rotated in the counter-clockwise direction from the resting position, the translating member 310 translates in a second direction opposite the first direction along a length of the shaft member 308. The translation of the translating member 310 in the second direction in turn drives or causes the ankle member 302 to rotate in the clockwise direction about the pivot point 306, adjusting the angle B between the lower limb member 302 and the foot unit 304. In an embodiment, this adjustment can bring the angle B between the lower limb member 302 and the foot unit 304 to a plantarflexion position.

Rotation of the foot unit 304 thus advantageously controls and/or drives rotation of the lower limb member 302 via axial movement of the translating member 310 along the shaft member 308. A large contact surface area is defined between the shaft member 308 and the translating member 310 and the lower limb member 302 and the translating member 310. Similar to the prosthesis 100, this allows the prosthesis 300 to distribute and handle greater loads than prior art prosthesis. It can also allow the prosthesis 300 to be made smaller and/or simpler than in the prior art. This can result in prosthesis that are less bulky, lighter-weight, and more natural to wear.

According to a variation, the prosthesis 300 can include an actuator arranged to provide the prosthesis 300 with the necessary energy to execute angular displacements between the lower limb member 302 and the foot unit 304. For instance, the actuator may cause the foot unit 304 to move similar to a natural human foot. The actuator can be a piston cylinder-type structure that pushes or pulls a posterior portion of the foot unit 304 with respect to the lower limb member 302. In other embodiments, the actuator may comprise other mechanisms capable of actively adjusting an angle, or providing for motion between, multiple members. For instance, the actuator may comprise a single-screw motor, a double-screw motor, a servomotor, a stepper motor, a rotary motor, a spring, a fluid actuator, or the like.

Figure 9:
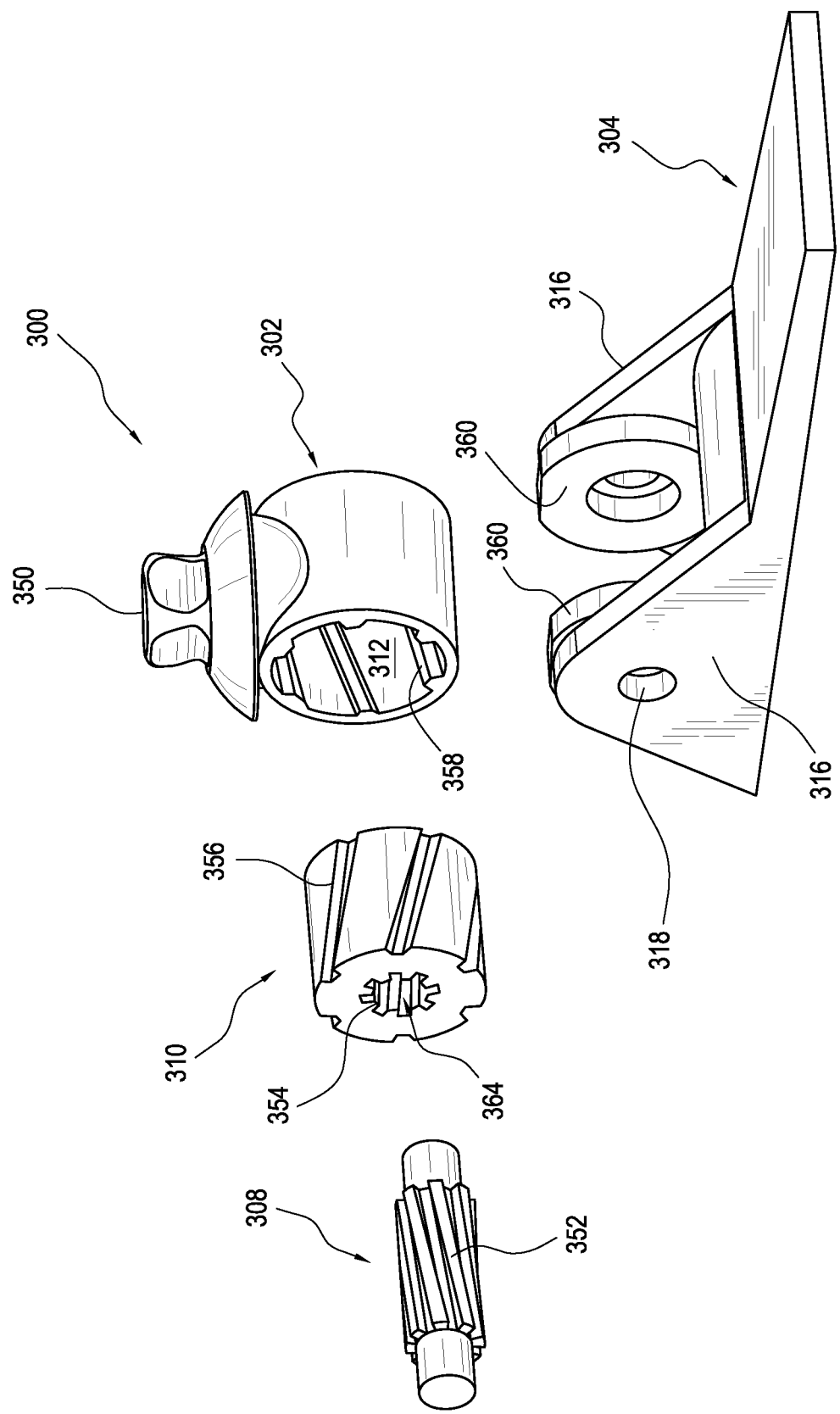
FIG. 9 is an exploded view of the movable joint in FIG. 6.

As seen in FIG. 9, the foot unit 304 can include a posterior portion defining upstanding support arm portions 316 on opposite sides of the lower limb member 302. A pair of opposing holes 318 are formed in the support arm portions 316. A portion of the upper surface of the foot unit 304 can define a curvature 362 (shown in FIG. 7) sized and configured to accommodate a lower area of the lower limb member 302 and its movement about the pivot point 306. The support arm portions 316 are sized such that a clearance is formed between the lower limb member 302 and the upper surface of the foot unit 304 when the lower limb member 302 is attached to the shaft member 308.

The shaft member 308 is connected to the foot unit 304 between the support arm portions 316. The shaft member 308 can be connected to the foot unit 304 via the holes 318. The shaft member 308 can be connected to the support arm portions 316 so that the shaft member 308 and the foot unit 304 rotate together.

The shaft member 308 defines a plurality of teeth 352 extending in an axial direction along a length the shaft member 308. The teeth 352 can be formed at an angle to the longitudinal axis of the shaft member 308 and can extend or curve along the shaft member 308. The teeth 352 can extend completely or along one or more portions of the shaft member 308. The teeth 352 can be generally helical.

The translating member 310 is attached to the shaft member 308 and positioned between the support arm portions 316 of the foot unit 304. The translating member 310 is adapted to move axially along the teeth 352 of the shaft member 308 when the shaft member 308 rotates. The translating member 310 is dimensioned and configured such that it can move in a back and forth direction between the support arm portions 316.

The translating member 310 is shown as a cylindrical body but can be any suitable member. The translating member 310 can define an internal gear 364 having a plurality of teeth 354 extending in the axial direction along of the bore 312. The teeth 354 are arranged to mesh or interact with the teeth 352 of the shaft member 308. The teeth 354 can be generally helical. When the translating member 310 is positioned in the receiving space 312, the translating member 310 is arranged not to rotate relative to the shaft member 308.

An outer surface of the translating member 310 also can define a plurality teeth 356 extending in the axial direction along the translating member 310. The teeth 356 can be formed at an angle to the longitudinal axis of the translating member 310 and can extend or curve along the translating member 310. The teeth 356 can be generally helical.

The lower limb member 302 is shown as a cylindrical sleeve defining an internal receiving space 312 for receiving or housing the translating member 310 and a portion of the shaft member 308. The axial length of the receiving space 312 is greater than the axial length of the translating member 310 such that one or more gaps are defined between at least one end of the receiving space 312 and at least one end of the translating member 310. These gaps vary as the translating member 310 moves along the shaft member 308 within the receiving space 312.

The receiving space 312 of the lower limb member 302 can define a plurality of teeth 358 extending in an axial direction along the receiving space 312. The teeth 358 are arranged to mesh or interact with the teeth 356 of the translating member 310. The teeth 358 have a different orientation than the teeth 356. Tooth loads between the translating member 310 and the lower limb member 302 create a driving force when the translating member 310 translates to rotate the lower limb member 302.

An upper surface of the lower limb member 302 can define a flat area for facilitating attachment of the attachment portion 350 to the lower limb member 302.

One or more spacers or washers 360 can be disposed between the support arm portions 316 of the foot unit 302 and the lower limb member 302. The spacers or washers 360 can help to properly align, space, and/or fasten components of the prosthesis 300. This can also help reduce friction between the lower limb member 302 and the foot unit 304.

As the translating member 310 moves along the axis of the shaft member 308, the interaction or tooth load between the teeth 356, 358 generates the driving force that rotates the lower limb member 302 about the pivot point 306. Rotation of the foot unit 304 thus advantageously controls and/or drives rotation of the lower limb member 302 via axial movement of the translating member 310.

The length, angle, depth, thickness, curvature, pressure angle, and/or pitch of the teeth and/or diameters of the translating member 310 and/or lower limb member 302 can at least in part define the range of motion of the prosthesis 300 and/or strength of the prosthesis 300 under a load.

When the internal teeth 354 of the translating member 310 are engaged with the teeth 352 of the shaft member 308, the teeth 354 are fully engaged along their length, providing an increased length of thread engagement. In addition, the internal teeth 354 are distributed circumferentially about the shaft member 308. This provides a solid connection between the shaft member 308 and the translating member 310 by increasing the surface contact area between them. This increased surface contact area also allows the prosthesis 300 to support and/or distribute greater loads. It facilitates control of the angular displacement between the foot unit 304 and the lower limb member 302. Similarly, the increased length of thread engagement between the translating member 310 and the lower limb member 302 also allows the prosthesis 300 to distribute greater loads and facilitates better control of the angular displacement between the foot unit 304 and the lower limb member 302.

In an embodiment, the prosthesis 300 is self-locking such that an input force applied to the lower leg limb member 302 will not move the foot unit 304. In other embodiments, the prosthesis 300 is not self-locking such that an input force applied to the lower limb member 302 will rotate the foot unit 304 and an input force applied to the foot unit 304 will rotate the lower limb member 302.

FIGS. 10-13 illustrate another embodiment of a movable joint comprising a knee joint or hinge 400. The hinge 400 includes a first joint section comprising a first hinge arm 402 and a second joint section comprising a second hinge arm 404. The first and second hinge arms 402, 404 are arranged to operatively connect the hinge 400 to an orthopedic device. For instance, a distal section of the first hinge arm 402 can be attached to a first strut of a knee brace and a proximal section of the second hinge arm 404 can be attached to a second strut of the knee brace.

Each of the hinge arms 402, 404 may be a bar or plate member and may be formed of metal, carbon fiber, plastic, or any other material which would provide sufficient strength to resist deformation during use.

A first shaft member 408 is non-rotatably connected at a first location point 482 to a distal section of the first hinge arm 402 and rotatably connected at a second location point 486 to a proximal section of the first link member 464. A second shaft member 466 can be non-rotatably connected at a third location point 490 to a proximal section of the second hinge arm 404 and rotatably connected at a fourth location point 494 to a distal section of the first link member 464.

A translating member 410 is attached to the first and second shaft members 408, 466. The translating member 410 is positioned within a receiving space 412 defined between the first link member 464 and the first and second hinge arms 402, 404. The translating member 410 is restrained from rotation so that rotation of the first shaft member 408 about a first pivot point 406 results in translation of the translating member 410 along a length of the first shaft member 408. The first shaft member 408 and the first pivot point 406 can be located on a same axis.

The translating member 410 also is attached to the second shaft member 466 so that when the translating member 410 translates along the first shaft member 408 it also translates along a length of the second shaft member 466, which, in turn, rotates the second shaft member 466 and the second hinge arm 404 about a second pivot point 472. The second shaft member 466 and the second pivot point 472 can be located on a same axis.

In another embodiment, the translating member 410 is arranged so that rotation of the second hinge arm 404 and the second shaft member 466 about the second pivot point 472 results in translation of the translating member 410 along the first and second shaft members 408, 466, which, in turn, rotates the first shaft member 408 and the first hinge arm 402 about the first pivot point 406. Optionally, the hinge 400 may include a cover 474 that houses and/or protects the components of the hinge 400.

The operation of the hinge 400 according to an embodiment will now be described in reference to FIGS. 11 and 12. When the first hinge arm 402 is rotated in a clockwise direction, the first shaft member 408 rotates with the first hinge arm 402 in the clockwise direction about the first pivot point 406. The rotation of the first shaft member 408 in the clockwise direction drives or causes the translating member 410 to translate in a first direction along a length of the first shaft member 408 and second shaft member 466. The translation of the translating member 410 in the first direction along the second shaft member 466 in turn drives or causes the second shaft member 466 and the second hinge arm 404 to rotate in a counter-clockwise direction about the second pivot point 472, decreasing the angle between the first and second hinge arms 402, 404.

In an embodiment, the hinge 400 can include an actuator arranged to provide it with the necessary energy to execute angular displacements between the first and second hinge arms 402, 404. For instance, the actuator may help control or actively adjust the angle between the first and second hinge arms 402, 404.

In an embodiment, the first and second shaft members 408, 466 can include helical teeth extending in opposite directions facilitating rotation of the first hinge arm 402 and the second hinge arm 404 in opposite directions. For instance, the first shaft member 408 can define a plurality of teeth 476 extending along a right-hand helix and the second shaft member 466 can define a plurality of teeth 478 extending along a left-hand helix or vice versa.

When the first hinge arm 402 is rotated in the counter-clockwise direction, the first shaft member 408 rotates with the first hinge arm 402 in the counter-clockwise direction about the first pivot point 406. The rotation of the first shaft member 408 in the counter-clockwise direction causes the translating member to translate in a second direction opposite the first direction along a length of the first and second shaft members 408, 466. The translation of the translating member 410 in the second direction along the second shaft member 466 in turn causes the second shaft member 466 and the second hinge arm 404 to rotate in the clockwise direction about the second pivot point 472, increasing the angle between the first and second hinge arms 402, 404. Rotation of one hinge arm thus advantageously controls and/or drives rotation of the other hinge arm via axial movement of the translating member 410 along the shaft members 408, 466.

It will be appreciated that the functional relationships between the components described are exemplary only as other relationships are possible. For instance, the functional relationships can be changed by varying the orientation of the helical teeth on one or more of the members, by reversing the direction of rotation, or by exchanging the positions of the first and second shaft members.

Figure 13:
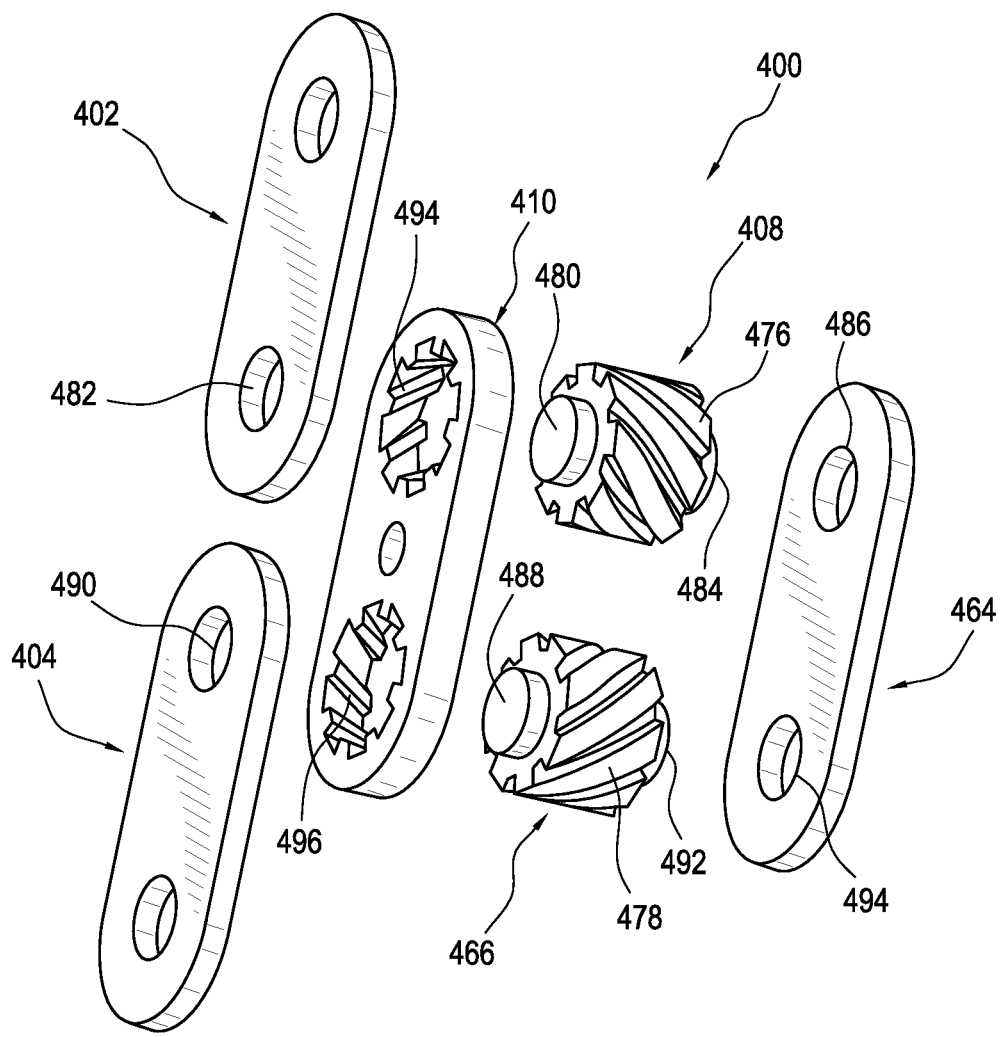
FIG. 13 is an exploded view of the movable joint in FIG. 10.

The first shaft member 408 can be attached to the first hinge arm 402 and the first link member 464 in any suitable manner. As seen in FIG. 13, the first shaft member 408 can be attached to the first hinge arm 402 at the first location point 482 via a protrusion 480 defined on the first shaft member 408 and positioned in a hole defined in the distal section of the first hinge arm 402. A second protrusion 484 opposite the first is arranged to extend into an opening formed in the first link member 464 to attach the first shaft member 408 to the first link member 464 at the second connection point 486. The teeth 476 can extend along all or some of the length of the first shaft member 408.

The second shaft member 466 can be attached to the second hinge arm 404 and the first link member 464 in any suitable manner. The second shaft member 466 can be attached to the second hinge arm 404 at the third location point 490 via a protrusion 488 defined on the second shaft member 466 positioned in a hole defined in the proximal section of the second hinge arm 404. A second protrusion 492 opposite the first protrusion is arranged to extend into an opening formed in the first link member 464 to attach the second shaft member 466 to the first link member 464 at the fourth location point 494. The teeth 478 can extend along all or some of the length of the second shaft member 466. As noted above, the teeth 478 can have a different orientation than the teeth 476.

The translating member 410 can comprise a second link member 410 connecting the first and second hinge arms 402, 404 together and/or the first and second shaft members 408, 466 together. The second link member 410 can define a first internal gear having a plurality of teeth 494 arranged to interact or mesh with the teeth 476 of the first shaft member 408. The teeth 494 can have a different orientation than the teeth 476. Tooth loads between the translating member 410 and the first shaft member 408 can translate the translating member 410 when the first shaft member 408 rotates.

The translating member 410 can also define a second internal gear having a plurality of teeth 496 arranged to interact or mesh with the teeth 478 of the second shaft member 466. The teeth 496 can be helical. Tooth loads between the second link member 410 and the second shaft member 466 created by translation of the translating member 410 can rotate the second shaft member 466.

To adjust the angular position between the first and second hinge arms 402, 404, one of the hinge arms is rotated with one of the shaft members relative to the other. This rotation causes the translating member 410 to translate along both of the shaft members, which in turn causes the other hinge arm and other shaft member to rotate.

Figures 14, 15:
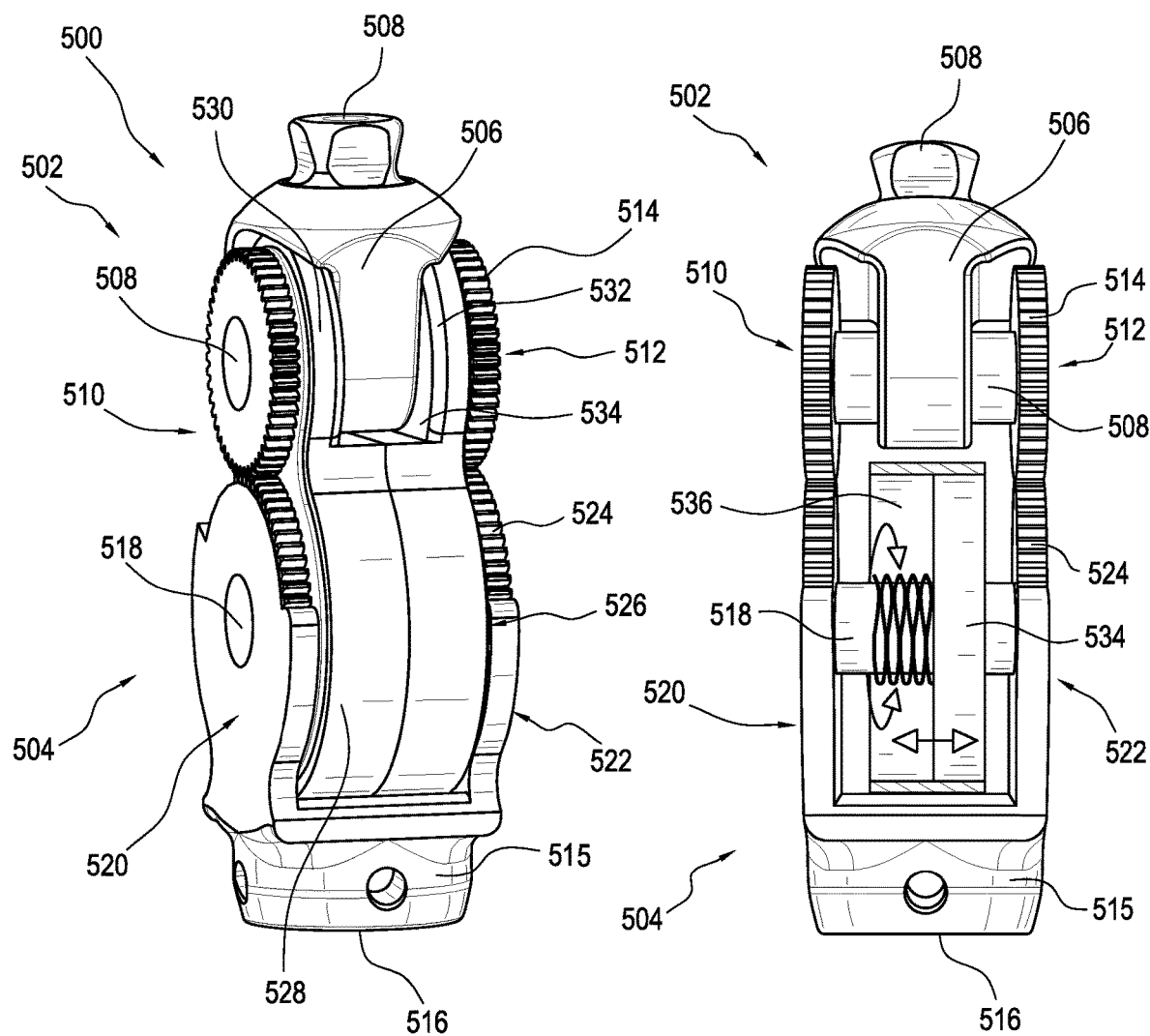
FIG. 14 is a perspective view of a movable joint according to another embodiment.
FIG. 15 is a front view of the movable joint of FIG. 14 with the cover removed for ease of reference.

FIGS. 14 and 15 show a movable joint 500 according to yet another embodiment. The movable joint 500 comprises a prosthetic knee joint including a first or upper joint section 502 and a second or lower joint section 504. The upper and lower joint sections 502, 504 are arranged to rotate relative to one another.

The upper joint section 502 includes an upper body portion 506 defining first connection portion 508 such as a pyramid connector. The first connection portion 508 can attach to a residual limb, to another prosthetic device, or to any other appropriate object. It will be appreciated that the first connection portion 508 can include attachment features other than a pyramid connector, such as a threaded hole or screw, a latch, a magnetic member, tube clamp, or other features.

The upper body portion 506 is attached to first shaft member 508 extending between first and second gears 510, 512. As seen, each of the first and second gears 510, 512 define a plurality of teeth 514. The first and second gears 510, 512 are shown comprising spur gears but can be any suitable type of gear.

The lower joint section 504 includes a lower body portion 515 defining a second connection portion 516. The second connection portion 516 can include a tube clamp attachment including a fastener for tightening. It will be appreciated that the second connection portion 516 can include attachment feature other than a tube clamp.

The lower body portion 515 is connected to a second shaft member 518 extending between third and fourth gears 520, 522. The third and fourth gears 520, 522 define a second plurality teeth 524 arranged to interact or mesh with the first teeth 514 of the first and second gears 510, 512. The interaction or meshing of the second teeth 524 of the lower joint section 504 with the first teeth 514 of the upper joint section 502 controls relative movement between the lower joint section 504 and the upper joint section 502. It will be appreciated that the gears can have any suitable shape.

The instantaneous center of rotation ("ICoR") of the lower joint section 504 is generally a point about which the lower joint section 504 rotates relative to the upper joint section 502. The location of the ICoR of the lower joint section 504 can depend on the relative sizes, profiles, and/or arrangements between the gears and the position of the first and second teeth 514, 524. It will be appreciated that the gears can have any suitable shape.

As the lower joint section 504 rotates relative to the upper joint section 502, the ICoR of the lower joint section 504 moves along a line extending through the first teeth 514 on the first and second gears 510, 512, generally corresponding to the profiles of the first and second gears 510, 512. It will be appreciated that the contact or interaction between the first and second teeth 514, 524 along the profiles of the gears can move the lower joint section 504 horizontally and/or vertically relative to the upper joint section 502 as the lower joint section 504 rotates relative to the upper joint section 502.

According to a variation, the profiles of the gears along the teeth can be selected or varied as needed to match a defined motion path. Additional exemplary details regarding the profiles of the gears along the teeth can be found in U.S. patent application Ser. No. 15/335,666, owned by the assignee of this disclosure and incorporated herein by reference.

A housing 526 connects the upper joint section 502 and the lower joint section 504. The housing 526 is located between the gears and extends between the upper and lower joint sections 502, 504. The housing 526 includes a main body 528 with a pair of flanges 530, 532 that protrude upwardly from the main body 528. The flanges 530, 532 can be generally parallel to each other and each can include a through hole arranged to accommodate the first shaft member 508. In the illustrated embodiment, the flanges 530, 532 are disposed on each side of the upper body portion 506 between the first and second gears 520, 522.

A clearance 534 is defined between the flanges 530, 532 for accommodating relative rotation between the housing 526 and the upper body portion 506. According to a variation, an under surface on the lateral and medial sides of the upper body portion 506 is curved or shaped to eliminate or minimize interference with the flanges 530, 532 as the upper body portion 506 rotates relative to the housing 526. The housing 526 further defines an internal cavity for receiving a translating member and cover member described below.

FIG. 15 shows the movable joint 500 with the housing 526 removed for ease of reference. A translating member 534 is threadedly attached to the second shaft member 518. The translating member 534 is positioned within a receiving space defined by a cover 536. According to an embodiment, the translating member 534 is restrained from rotation so that translation of the translating member 534 results in rotation of the second shaft member 518, which, in turn, rotates the lower joint section 504.

The operation of the movable joint 500 according to an embodiment will now be described. When the translating member 534 translates in a first direction along a length of the second shaft member 518 within the cover 536, the interaction between the translating member 534 and the second shaft member 518 causes or drives the second shaft member 518 to rotate in a counter-clockwise direction, which, in turn, rotates the lower joint section 504 in the counter-clockwise direction. In an embodiment, the second shaft member 518, the lower body portion 515 and the housing 526 rotate together. This can adjust an angle between the upper joint section 502 and the lower joint section 504. In an embodiment, this adjustment can bring the angle between the upper joint section 502 and the lower joint section 504 to a flexion position.

When the translating member 534 translates in a second direction opposite the first direction along a length of the second shaft member 518, the interaction between the translating member 534 and the second shaft member 518 causes or drives the second shaft member 518 to rotate in a clockwise direction, which, in turn, adjusts the angle between the upper joint section 502 and the lower joint section 504. In an embodiment, this adjustment can bring the angle between the upper joint section 502 and the lower joint section 504 toward an extension or stance position.

Axial movement of the translating member 534 along the second shaft member 518 thus advantageously controls and/or drives relative rotation between the lower joint section 504 and the upper joint section 502.

In an embodiment, the movable joint 500 can include an actuator arranged to provide the movable joint 500 with the necessary energy to execute angular displacements between the upper joint section 502 and the lower joint section 504. The actuator can be a pump system or any other suitable system arranged to drive translation of the translating member 534 along the second shaft member 518 in the first and/or second directions, which, in turn drives movement of the lower joint section 504 relative to the upper joint section 502.

It will be appreciated that the movable joints described are to be regarded as exemplary only, as other joint assemblies are possible. For instance, the movable joint can include one, two, three, or any other suitable number of pivot points. In other embodiments, the shaft member can be attached to a central member and the translating member can define teeth on opposing sides of the translating member. The first and second joint sections can be pivotally attached to opposing sides of the central member. The first and second joint sections can each define a plurality of teeth arranged to mesh with the teeth of the central member. As such, when the translating member is driven along a length of the shaft member, the engagement between the translating member and the first and second joint sections drives rotation of both the first and second joint sections. In other embodiments, the shaft member and/or translating member may have larger diameters. In other embodiments, the translating member and/or second hinge arm can have more or less teeth or different helix angles. Moreover, while helical teeth are described, it will be appreciated that other gearing and/or thread arrangements are possible to rotate at least one of the joint sections upon axial movement of the translating member.

While various aspects and embodiments have been disclosed herein, other aspects and embodiments are contemplated. The various aspects and embodiments disclosed herein are for purposes of illustration and are not intended to be limiting. Additionally, the words "including," "having," and variants thereof (e.g., "includes" and "has") as used herein, including the claims, shall be open ended and have the same meaning as the word "comprising" and variants thereof (e.g., "comprise" and "comprises").

The invention claimed is:

1. A movable joint for use in a prosthetic or orthopedic system, the movable joint comprising:
    first and second joint sections arranged to rotate relative to one another about a pivot point having a rotational axis;
    a shaft member attached to the first joint section, the shaft member being coaxial with the rotational axis of the pivot point;
    a translating member attached to the shaft member, wherein translation of the translating member occurs along the rotational axis and the shaft member drives rotation of the second joint section;
    wherein the translating member defines a bore extending therethrough and coaxial to the rotational axis, the translating member defining internal gear teeth along a circumference and length of the bore, said internal gear teeth arranged in a helical configuration;
    wherein the shaft member defines a plurality of teeth in a helical configuration along a majority of a length and circumference of the shaft member, the helical configuration being arranged helically to a longitudinal axis of the shaft member coaxial to the rotational axis;
    wherein the internal gear teeth of the translating member are fully engaged to the plurality of teeth of the shaft member in that the internal gear teeth are distributed circumferentially about the plurality of teeth of the shaft member;
    wherein the second joint section defines a receiving space and the translating member is positioned in the receiving space of the second joint section, the translating member being restrained from rotation within the receiving space;
    wherein the length of the shaft member is greater than the length of the bore;
    further comprising an actuator arranged to provide the movable joint with energy to execute angular displacements between the first and second joint sections about the pivot point, wherein the actuator is arranged to controllably drive rotation of the shaft member and interaction between the translating member and the shaft member is arranged such that the actuator continuously adjusts the movable joint within a predetermined range of motion;
    wherein the actuator includes a pump system arranged to drive translation of the translating member within a housing forming a portion of the second joint section, the receiving space being defined within the housing;
    wherein the pump system includes a first pump unit and a second pump unit, and the receiving space defines a first fluid chamber on a first side of the translating member and a second fluid chamber on a second side of the translating member opposite the first side of the translating member.

2. The movable joint of claim 1, wherein the movable joint is self-locking such that an angle defined between the first and second joint sections is only adjustable via an input torque applied to the shaft member.

3. The movable joint of claim 1, wherein the first joint section comprises a lower limb member and the second joint section comprises a foot unit.

4. The movable joint of claim 3, wherein the lower limb member is coupled to the foot unit at the pivot point defined by the shaft member.

5. The movable joint of claim 1, wherein the housing defines first and second openings in fluid communication with the first fluid chamber and third and fourth openings in fluid communication with the second fluid chamber, the first pump unit is fluidly attached to the first opening and the second pump unit is fluidly attachable to the third opening.

6. The movable joint of claim 5, wherein the first and second pump units are attached to the housing, the first and second fluid chambers and the first and second openings at least in part define a sealed volume arranged to contain a fluid.

7. A movable joint for use in a prosthetic or orthopedic system, the movable joint comprising:
    first and second joint sections arranged to rotate relative to one another about a pivot point having a rotational axis;
    a shaft member attached to the first joint section and arranged to rotate relative to the second joint section, the shaft member being coaxial with the rotational axis of the pivot point; and
    a translating member attached to the shaft member and engaging with the second joint section,
    wherein rotation of the shaft member drives the translating member axially along a length of the shaft member and translation of the translating member occurs along the rotational axis and the shaft member drives rotation of the second joint section relative to the first joint section;
    wherein the translating member defines a bore extending therethrough and coaxial to the rotational axis, the translating member defining internal gear teeth along a circumference and length of the bore, said internal gear teeth arranged in a helical configuration;
    wherein the shaft member defines a plurality of teeth in a helical configuration along a majority of the length and circumference of the shaft member, the helical configuration being arranged helically to a longitudinal axis of the shaft member coaxial to the rotational axis;
    wherein the internal gear teeth of the translating member are fully engaged to the plurality of teeth of the shaft member in that the internal gear teeth are distributed circumferentially about the plurality of teeth of the shaft member;

wherein the second joint section defines a receiving space and the translating member is fittingly positioned in the receiving space of the second joint section, the translating member being restrained from rotation within the receiving space, and the shaft member rotates relative to the translating member;

wherein the length of the shaft member is greater than the length of the bore;

further comprising an actuator arranged to provide the movable joint with energy to execute angular displacements between the first and second joint sections about the pivot point, wherein the actuator is arranged to controllably drive rotation of the shaft member and interaction between the translating member and the shaft member is arranged such that the actuator continuously adjusts the movable joint within a predetermined range of motion;

wherein the actuator includes a pump system arranged to drive translation of the translating member within a housing forming a portion of the second joint section, the receiving space being defined within the housing;

wherein the pump system includes a first pump unit and a second pump unit, and the receiving space defined a first fluid chamber on a first side of the translating member and a second fluid chamber on a second side of the translating member opposite the first side of the translating member.

8. The movable joint of claim 7, wherein the housing defines first and second openings in fluid communication with the first fluid chamber and third and fourth openings in fluid communication with the second fluid chamber, the first pump unit is fluidly attached to the first opening and the second pump unit is fluidly attachable to the third opening.

9. The movable joint of claim 8, wherein the first and second pump units are attached to the housing, the first and second fluid chambers and the first and second openings at least in part define a sealed volume arranged to contain a fluid.

\* \* \* \* \*